(12) United States Patent
Chiang et al.

(10) Patent No.: US 8,080,050 B2
(45) Date of Patent: Dec. 20, 2011

(54) PROSTHESIS DELIVERY SYSTEMS AND METHODS

(75) Inventors: Andrew L. Chiang, Fremont, CA (US); Lee Bolduc, Sunnyvale, CA (US)

(73) Assignee: Aptus Endosystems, Inc., Sunnyvale, CA (US)

( * ) Notice: Subject to any disclaimer, the term of this patent is extended or adjusted under 35 U.S.C. 154(b) by 661 days.

(21) Appl. No.: 11/633,724

(22) Filed: Dec. 5, 2006

(65) Prior Publication Data

US 2007/0083255 A1   Apr. 12, 2007

Related U.S. Application Data

(63) Continuation of application No. 10/692,283, filed on Oct. 23, 2003, now Pat. No. 7,147,657.

(60) Provisional application No. 60/488,753, filed on Jul. 21, 2003.

(51) Int. Cl.
*A61F 2/06* (2006.01)

(52) U.S. Cl. ........................................ 623/1.11

(58) Field of Classification Search .......... 606/191–198; 623/1.1, 1.11–1.13, 1.2, 1.23
See application file for complete search history.

(56) References Cited

U.S. PATENT DOCUMENTS

| | | | |
|---|---|---|---|
| 2,033,039 A | 3/1936 | Limpert | |
| 3,499,222 A | 3/1970 | Linkow et al. | |
| 3,686,740 A | 8/1972 | Shiley | |
| 3,799,172 A | 3/1974 | Szpur | |
| 4,140,126 A | 2/1979 | Choudhury | |
| 4,307,722 A | 12/1981 | Evans | |
| 4,580,568 A | 4/1986 | Gianturco | |
| 4,625,597 A | 12/1986 | Cast | |
| 4,781,682 A | 11/1988 | Patel | |
| 4,898,577 A | 2/1990 | Badger et al. | |
| 4,921,484 A | 5/1990 | Hillstead | |
| 4,990,151 A | 2/1991 | Wallsten | |
| 5,030,204 A | 7/1991 | Badger et al. | |
| 5,042,707 A | 8/1991 | Taheri | |
| 5,071,407 A | 12/1991 | Termin et al. | |
| 5,104,399 A | 4/1992 | Lazarus | |
| 5,207,695 A | 5/1993 | Trout, III | |
| 5,282,824 A | 2/1994 | Gianturco | |
| 5,290,295 A | 3/1994 | Querals et al. | |
| 5,330,490 A | 7/1994 | Wilk et al. | |
| 5,330,503 A | 7/1994 | Yoon | |

(Continued)

FOREIGN PATENT DOCUMENTS

EP   0 321 912 A1   6/1989

(Continued)

OTHER PUBLICATIONS

Anonymous. (1995). "5mm Origin Tacker™ It Runs In Circles Around Staples," *Guidant Origin Advertising Literature*, 2 pages.

(Continued)

*Primary Examiner* — Kevin T Truong
(74) *Attorney, Agent, or Firm* — Morrison & Foerster LLP

(57) ABSTRACT

Apparatus and method deliver a prosthesis into a hollow body organ or blood vessel. The systems and methods make use of a catheter. A carrier on the distal end of the catheter is sized and configured to carry the prosthesis. A release mechanism and an enclosure mechanism on the distal end are operable to retain and enclose the prosthesis on the carrier. The release mechanism and the enclosure mechanism are also operable to selectively expose and release the prosthesis from the carrier for deployment in the hollow body organ or blood vessel.

2 Claims, 15 Drawing Sheets

U.S. PATENT DOCUMENTS

| | | | |
|---|---|---|---|
| 5,387,235 A | 2/1995 | Chuter |
| 5,456,713 A | 10/1995 | Chuter |
| 5,456,714 A | 10/1995 | Owen |
| 5,470,337 A | 11/1995 | Moss |
| 5,480,382 A | 1/1996 | Hammerslag et al. |
| 5,480,423 A | 1/1996 | Ravenscroft et al. |
| 5,489,295 A | 2/1996 | Piplani et al. |
| 5,531,686 A | 7/1996 | Lundquist et al. |
| 5,534,007 A | 7/1996 | St. Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A | 12/1996 | Bolduc et al. |
| 5,609,627 A | 3/1997 | Goicoechea et al. |
| 5,626,613 A | 5/1997 | Schmieding |
| 5,639,278 A | 6/1997 | Dereume et al. |
| 5,662,675 A | 9/1997 | Polanskyj Stockert et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | McDonald |
| 5,683,450 A | 11/1997 | Goicoechea et al. |
| 5,693,084 A | 12/1997 | Chuter |
| 5,693,086 A | 12/1997 | Goicoechea et al. |
| 5,700,269 A | 12/1997 | Pinchuk et al. |
| 5,702,365 A | 12/1997 | King |
| 5,707,376 A | 1/1998 | Kavteladze et al. |
| 5,713,907 A | 2/1998 | Hogendijk et al. |
| 5,733,325 A | 3/1998 | Robinson et al. |
| 5,749,921 A | 5/1998 | Lenker et al. |
| 5,755,777 A | 5/1998 | Chuter |
| 5,776,142 A | 7/1998 | Gunderson |
| 5,810,882 A | 9/1998 | Bolduc et al. |
| 5,814,016 A | 9/1998 | Valley et al. |
| 5,824,008 A | 10/1998 | Bolduc et al. |
| 5,824,041 A | 10/1998 | Lenker et al. |
| 5,830,229 A | 11/1998 | Konya et al. |
| 5,855,565 A | 1/1999 | Bar-Cohen et al. |
| 5,876,432 A | 3/1999 | Lau et al. |
| 5,906,619 A | 5/1999 | Olson et al. |
| 5,916,263 A | 6/1999 | Goicoechea et al. |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 6,024,763 A | 2/2000 | Lenker et al. |
| 6,070,589 A | 6/2000 | Keith et al. |
| 6,086,582 A | 7/2000 | Altman et al. |
| 6,123,722 A | 9/2000 | Fogarty et al. |
| 6,126,685 A | 10/2000 | Lenker et al. |
| 6,145,509 A | 11/2000 | Tanner |
| 6,146,339 A | 11/2000 | Biagtan et al. |
| 6,203,550 B1 | 3/2001 | Olson |
| 6,217,597 B1 | 4/2001 | Tanner |
| 6,248,118 B1 | 6/2001 | Tanner et al. |
| 6,258,119 B1 | 7/2001 | Hussein et al. |
| 6,270,516 B1 | 8/2001 | Tanner et al. |
| 6,287,315 B1 | 9/2001 | Wijeratne et al. |
| 6,296,656 B1 | 10/2001 | Bolduc et al. |
| 6,302,906 B1 | 10/2001 | Goicoechea et al. |
| 6,336,933 B1 | 1/2002 | Parodi |
| 6,346,118 B1 | 2/2002 | Baker et al. |
| 6,371,919 B1 | 4/2002 | Tanner et al. |
| 6,409,757 B1 | 6/2002 | Trout, III et al. |
| 6,428,565 B1 | 8/2002 | Wisselink |
| 6,458,152 B1 | 10/2002 | Khosravi et al. |
| 6,520,974 B2 | 2/2003 | Tanner et al. |
| 6,544,253 B1 | 4/2003 | Tanner |
| 6,562,051 B1 | 5/2003 | Bolduc et al. |
| 6,592,593 B1 | 7/2003 | Parodi et al. |
| 6,607,555 B2 | 8/2003 | Patterson et al. |
| 6,639,278 B2 | 10/2003 | Sumida et al. |
| 6,652,572 B2 | 11/2003 | Kugler et al. |
| 6,730,119 B1 | 5/2004 | Smalling |
| 6,800,081 B2 | 10/2004 | Parodi |
| 6,878,164 B2 | 4/2005 | Kujawski et al. |
| 7,081,129 B2 | 7/2006 | Chobotov |
| 7,147,657 B2 | 12/2006 | Chiang et al. |
| 7,306,623 B2 | 12/2007 | Watson |
| 7,637,932 B2 | 12/2009 | Bolduc et al. |
| 2002/0099432 A1 | 7/2002 | Yee |
| 2003/0233140 A1 | 12/2003 | Hartley et al. |
| 2004/0093057 A1 | 5/2004 | Bolduc et al. |
| 2004/0138734 A1 | 7/2004 | Chobotov et al. |
| 2006/0259125 A1 | 11/2006 | Peacock, III |
| 2007/0032860 A1 | 2/2007 | Brooks et al. |
| 2007/0073389 A1 | 3/2007 | Bolduc et al. |
| 2008/0065189 A1 | 3/2008 | Bolduc |
| 2008/0097489 A1 | 4/2008 | Goldfarb et al. |
| 2008/0132996 A1 | 6/2008 | Drasler et al. |
| 2009/0112302 A1 | 4/2009 | Stafford |
| 2010/0094400 A1 | 4/2010 | Bolduc et al. |

FOREIGN PATENT DOCUMENTS

| | | |
|---|---|---|
| EP | 0 663 184 A1 | 7/1995 |
| EP | 1 369 098 | 12/2003 |
| EP | 1 440 673 | 7/2004 |
| FR | 2299548 A1 | 8/1976 |
| WO | WO-97/03616 A1 | 2/1997 |
| WO | WO 98/53761 | 12/1998 |
| WO | WO-99/53845 A1 | 10/1999 |
| WO | WO-03/045283 A1 | 6/2003 |
| WO | WO-03/045467 A2 | 6/2003 |
| WO | WO-03/045467 A3 | 6/2003 |
| WO | WO-03/079935 A1 | 10/2003 |
| WO | WO-2005/04407 A3 | 5/2005 |
| WO | WO-2005/044073 A2 | 5/2005 |
| WO | WO-2005/044073 A3 | 5/2005 |
| WO | WO-2007/046955 A2 | 4/2007 |
| WO | WO-2007/046955 A3 | 4/2007 |
| WO | WO-2010/044855 A1 | 4/2010 |

OTHER PUBLICATIONS

Gadacz, T. et al. (Nov. 1995). "The Spiral Tacker: A New Technique for Stabilizing Prosthetic Mesh in Laparoscopic Hernia Repair," *Surgical Rounds* 461-467.

Hatchett, R.L. et al. (1995). "Extraperitoneal Endoscopic Burch Repair Using a Tacker Mesh Technique," *Circa* 1-4.

Medical Technologies. (Oct. 1995). "Laparoscopic Surgery," *Medical Data International, Inc. MedPro* p. 190.

Newman, L. et al. (1995). "Tacker-Assisted TAPP Procedure," *Circa*, 2 pages.

Non-Final Office Action mailed May 14, 2008, for U.S. Appl. No. 11/255,116, filed Oct. 20, 2005, 14 pages.

Notice of Allowance mailed Aug. 10, 2009, for U.S. Appl. No. 11/255,116, filed Oct. 20, 2005, 4 pages.

Non Final Office Action mailed on Nov. 16, 2005, for U.S. Appl. No. 10/692,283, 5 pages.

Notice of Allowance mailed on Aug. 1, 2006, for U.S. Appl. No. 10/692,283, 4 pages.

International Search Report mailed on Mar. 6, 2003, for PCT Patent Application No. PCT/US02/32753, filed on Oct. 15, 2002, published on Jun. 5, 2003, as WO 2003/045283, one page.

Written Opinion mailed on Aug. 26, 2003, for PCT Patent Application No. PCT/US02/32753, filed on Oct. 15, 2002, published on Jun. 5, 2003, as WO 2003/045283, 4 pages.

International Preliminary Report on Patentability mailed on Sep. 1, 2004, for PCT Patent Application No. PCT/US02/32753, filed on Oct. 15, 2002, published on Jun. 5, 2003, as WO 2003/045283, 3 pages.

International Search Report mailed on May 8, 2003, for PCT Patent Application No. PCT/US02/38365, filed on Nov. 29, 2002, published on Jun. 5, 2003, as WO 2003/045467, 4 pages.

Written Opinion mailed on Oct. 27, 2003, for PCT Patent Application No. PCT/US02/38365, filed on Nov. 29, 2002, published on Jun. 5, 2003, as WO 2003/045467, 4 pages.

International Preliminary Report on Patentability mailed on Mar. 1, 2004, for PCT Patent Application No. PCT/US02/38365, filed on Nov. 29, 2002, published on Jun. 5, 2003, as WO 2003/045467, 3 pages.

International Search Report mailed on Aug. 15, 2007, for PCT Patent Application No. PCT/US06/033749, filed on Aug. 29, 2006, published on Apr. 26, 2007, as WO 2007/046955, 3 pages.

Written Opinion mailed on Aug. 15, 2007, for PCT Patent Application No. PCT/US06/033749, filed on Aug. 29, 2006, published on Apr. 26, 2007, as WO 2007/046955, 5 pages.

International Preliminary Report on Patentability mailed on Jun. 18, 2008, for PCT Patent Application No. PCT/US06/033749, filed on Aug. 29, 2006, published on Apr. 26, 2007, as WO 2007/046955, 6 pages.

International Search Report mailed on Dec. 27, 2005, for PCT Patent Application No. PCT/US2004/027587, filed on Aug. 25, 2004, published on May 19, 2005, as WO 2005/044073, 2 pages.

Written Opinion mailed on Dec. 27, 2005, for PCT Patent Application No. PCT/US2004/027587, filed on Aug. 25, 2004, published on May 19, 2005, as WO 2005/044073, 3 pages.

International Preliminary Report on Patentability mailed on May 24, 2006, for PCT Patent Application No. PCT/US2004/027587, filed on Aug. 25, 2004, published on May 19, 2005, as WO 2005/044073, 3 pages.

International Search Report mailed on Dec. 10, 2009, for PCT/US2009/005608, filed Oct. 14, 2009, published on Apr. 22, 2010, as WO 2010/044855, 3 pages.

Written Opinion mailed on Dec. 10, 2009, for PCT/US2009/005608, filed Oct. 14, 2009, published on Apr. 22, 2010, as WO 2010/044855, 4 pages.

PROSTHESIS DELIVERY SYSTEMS AND METHODS

RELATED APPLICATIONS

This application is a continuation of U.S. patent application Ser. No. 10/692,283 filed 23 Oct. 2003, now U.S. Pat. No. 7,147,657, which in turn claims the benefit of U.S. Provisional patent application Ser. No. 60/488,753, filed Jul. 21, 2003, and entitled "Endoprosthesis Delivery Systems and Methods."

FIELD OF THE INVENTION

The invention relates generally to the delivery of a prosthesis to a targeted site within the body, e.g., for the repair of diseased and/or damaged sections of a hollow body organ and/or blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta primarily occur in abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic prosthesis, made either in a straight of bifurcated configuration, is installed and then permanently attached and sealed to the ends of the native vessel by suture. The prosthetic prosthesis for these procedures are usually unsupported woven tubes and are typically made from polyester, ePTFE or other suitable materials. The prosthesis are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prosthetic prostheses for aortic aneurysms are delivered collapsed on a catheter through the femoral artery. These prostheses are usually designed with a fabric material attached to a metallic scaffolding (stent) structure, which expands or is expanded to contact the internal diameter of the vessel. Unlike open surgical aneurysm repair, intraluminally deployed prostheses are not sutured to the native vessel, but rely on either barbs extending from the stent, which penetrate into the native vessel during deployment, or the radial expansion force of the stent itself is utilized to hold the prosthesis in position. These prosthesis attachment means do not provide the same level of attachment when compared to suture and can damage the native vessel upon deployment.

SUMMARY OF THE INVENTION

One aspect of the invention provides apparatus and methods for delivering a prosthesis into a hollow body organ or blood vessel. The systems and methods include a catheter that is sized and configured for introduction into the hollow body organ or blood vessel. A carrier on the distal end of the catheter is sized and configured to carry the prosthesis. A release mechanism on the distal end is operable to retain the prosthesis on the carrier. The release mechanism is also operable to selectively release the prosthesis from the carrier for deployment in the hollow body organ or blood vessel. An enclosure mechanism on the distal end is operable to enclose the prosthesis on the carrier. The enclosure mechanism is also operable to selectively expose the prosthesis on the carrier, to thereby enable the release of the prosthesis from the carrier in response to selective operation of the release mechanism, which can occur separate from the operation of the enclosure mechanism or in conjunction with the enclosure mechanism. The systems and methods include at least one actuator, which is coupled to the release mechanism and the enclosure mechanism, to selectively operate the release mechanism and the enclosure mechanism, either separately or in conjunction.

Other features and advantages of the invention shall be apparent based upon the accompanying description, drawings, and claims.

BRIEF DESCRIPTION OF THE DRAWINGS

The invention will be understood from the following detailed description of preferred embodiments, taken in conjunction with the accompanying drawings, wherein.

DETAILED DESCRIPTION OF THE INVENTION

I. Prosthesis Delivery Catheter

Figure 1:
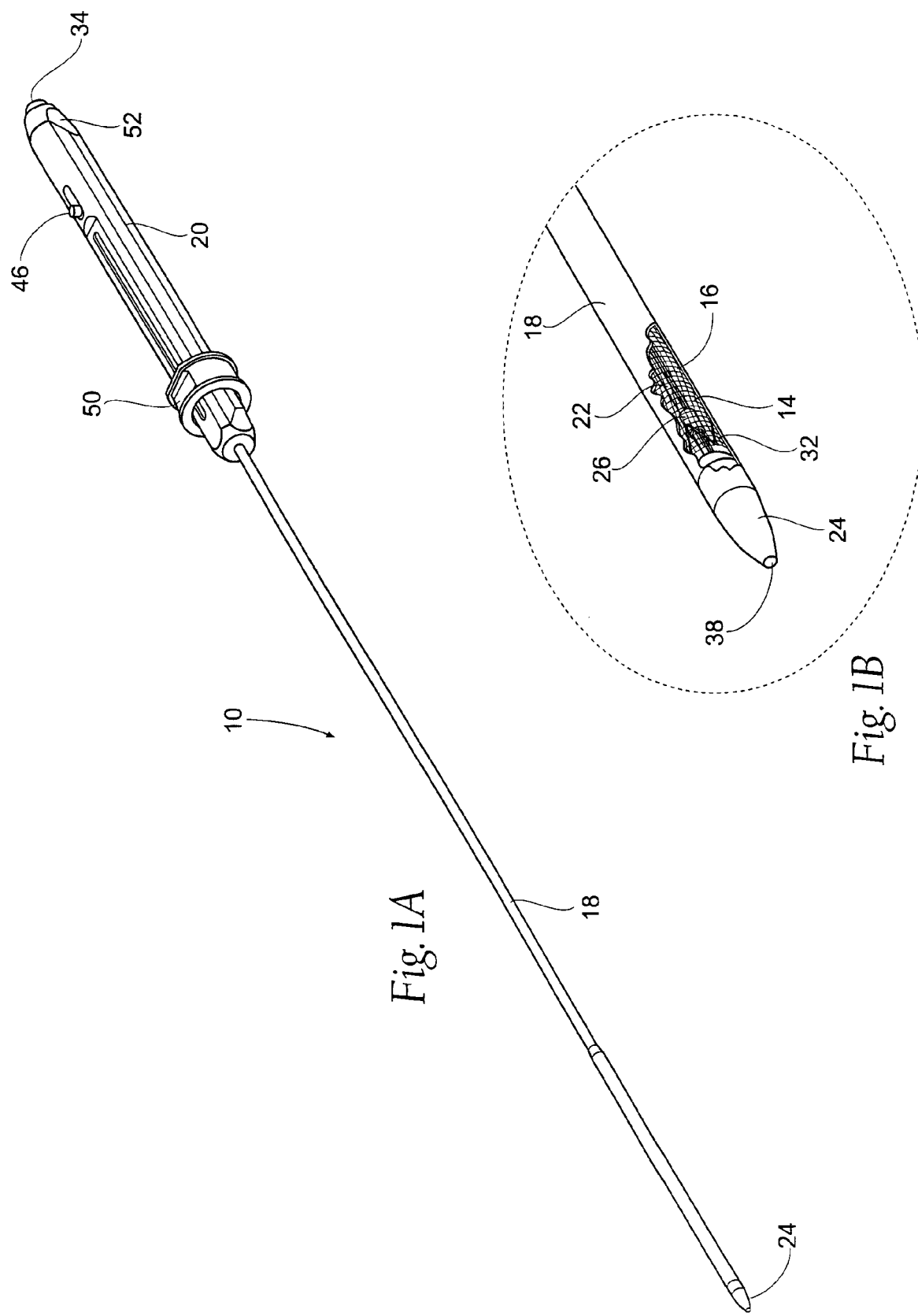
FIG. 1A is a perspective view of a prosthesis delivery catheter embodies features of the invention.
FIG. 1B is an enlarged perspective view, with portions broken away and in section, of the distal end of the prosthesis delivery catheter shown in FIG. 1A.

FIGS. 1A and 1B show a prosthesis delivery catheter 10. The purpose of the catheter 10 is to (i) contain and/or restrain a prosthesis 14 prior to its deployment (see FIG. 1B), (ii) deliver the prosthesis 14 through the vasculature to a desired location within the body, e.g., a hollow body organ or a blood vessel (see FIG. 2), and (iii) controllably deploy the prosthesis 14 in the desired location (see FIG. 3).

In the illustrated arrangement (see FIG. 3), the prosthesis 14 takes the form of an endovascular, self-expanding stent prosthesis. In this respect, the prosthesis or prostheses 14 may have a wide variety of conventional configurations. It can typically comprise a fabric or some other blood semi-impermeable flexible barrier which is supported by a structure formed by stents 48. The stent structure can have any conventional stent configuration, such as zigzag, serpentine, expanding diamond, or combinations thereof. The stent structure may extend the entire length of the prosthesis, and in some instances can be longer than the fabric components of the prosthesis. Alternatively, the stent structure can cover only a small portion of the prosthesis, e.g., being present at the ends. The stent structure may have three or more ends when it is configured to treat bifurcated vascular regions, such as the treatment of abdominal aortic aneurysms, when the stent prosthesis extends into the iliac arteries. In certain instances, the stent structures can be spaced apart along the entire length, or at least a major portion of the entire length, of the stent-prosthesis, where individual stent structures are not connected to each other directly, but rather connected to the fabric or other flexible component of the prosthesis. Still, it is contemplated that the stent structures could be attached to one another at discrete locations, e.g., in the proximal neck region. Such stent structures could comprise individual stents that are connected together when incorporated into the prosthesis, or stents that are manufactured in a joined condition prior to incorporation into the prosthesis.

The stents 48 may be elastic, e.g., comprised of a shape memory alloy elastic stainless steel, or the like. For elastic, expanding typically comprises releasing the stent structure from a constraint to permit the stent structure to self-expand at the implantation site. As will be described in greater detail, the catheter 10 places a sheath over the stent structure, in combination with releasable restraining means coupled to the stent structure, to maintain the stent structure in a radially reduced configuration during passage into the body. In this arrangement, self-expansion of the stent structure is achieved by pulling back on the sheath and release of the restraining means, to permit the stent structure to assume its larger diameter configuration.

Alternatively, the stent structure may be formed from a malleable material, such as malleable stainless steel of other metals. Expansion may then comprise applying a radially expansive force within the structure to cause expansion, e.g., inflating a delivery catheter within the stent structure in order to affect the expansion. In this arrangement, the positioning and deployment of the endoprosthesis can be accomplished by the use of an expansion means either separate or incorporated into the deployment catheter. This will allow the endoprosthesis to be positioned within the vessel and partially deployed while checking relative position within the vessel. The expansion can be accomplished either via a balloon or mechanical expansion device. Additionally, this expansion stabilizes the position of the endoprosthesis within the artery by resisting the force of blood on the endoprosthesis until the endoprosthesis can be fully deployed. Still, alternatively, the stent structure may comprise a combination of a self-expanding stent and a malleable stent structure.

In the illustrated embodiment (see FIG. 2), the catheter 10 is shown it is being positioned over a guidewire 12 in a body lumen. The catheter 10 carries the prosthesis 14 in a radially reduced configuration to a targeted site. At the targeted site, the catheter 10 releases the radially reduced prosthesis 14, which expands radially (see FIG. 3). After partial or complete expansion or deployment of the prosthesis 14, one or more fasteners are desirably introduced by a fastener attachment assembly to anchor the prosthesis 14 in place. Further details of the fastener attachment assembly can be found in U.S. patent application Ser. No. 10/307,226, filed Nov. 29, 2002, which is incorporated herein by reference.

Figure 3:
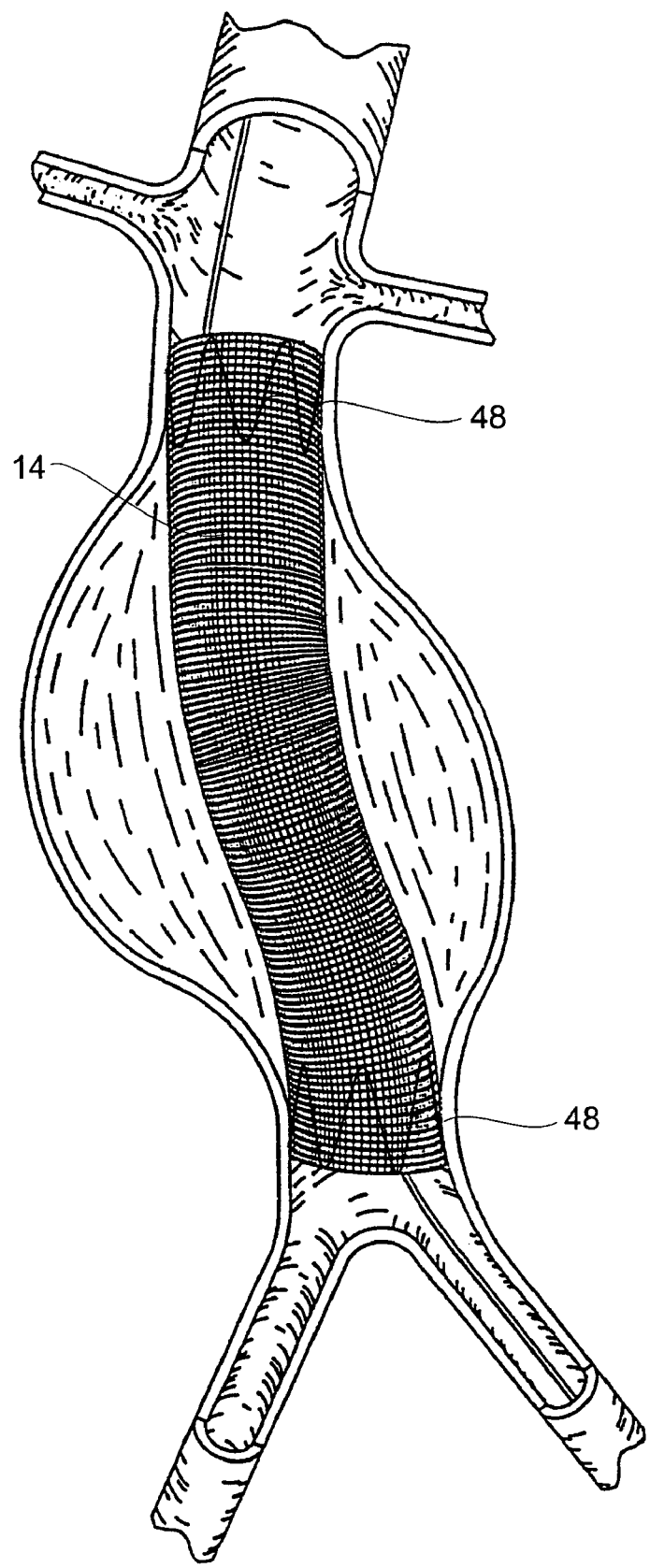
FIG. 3 is a perspective view of a straight endovascular prosthesis after deployment by the prosthesis delivery catheter shown in FIG. 1A.
Figure 4:
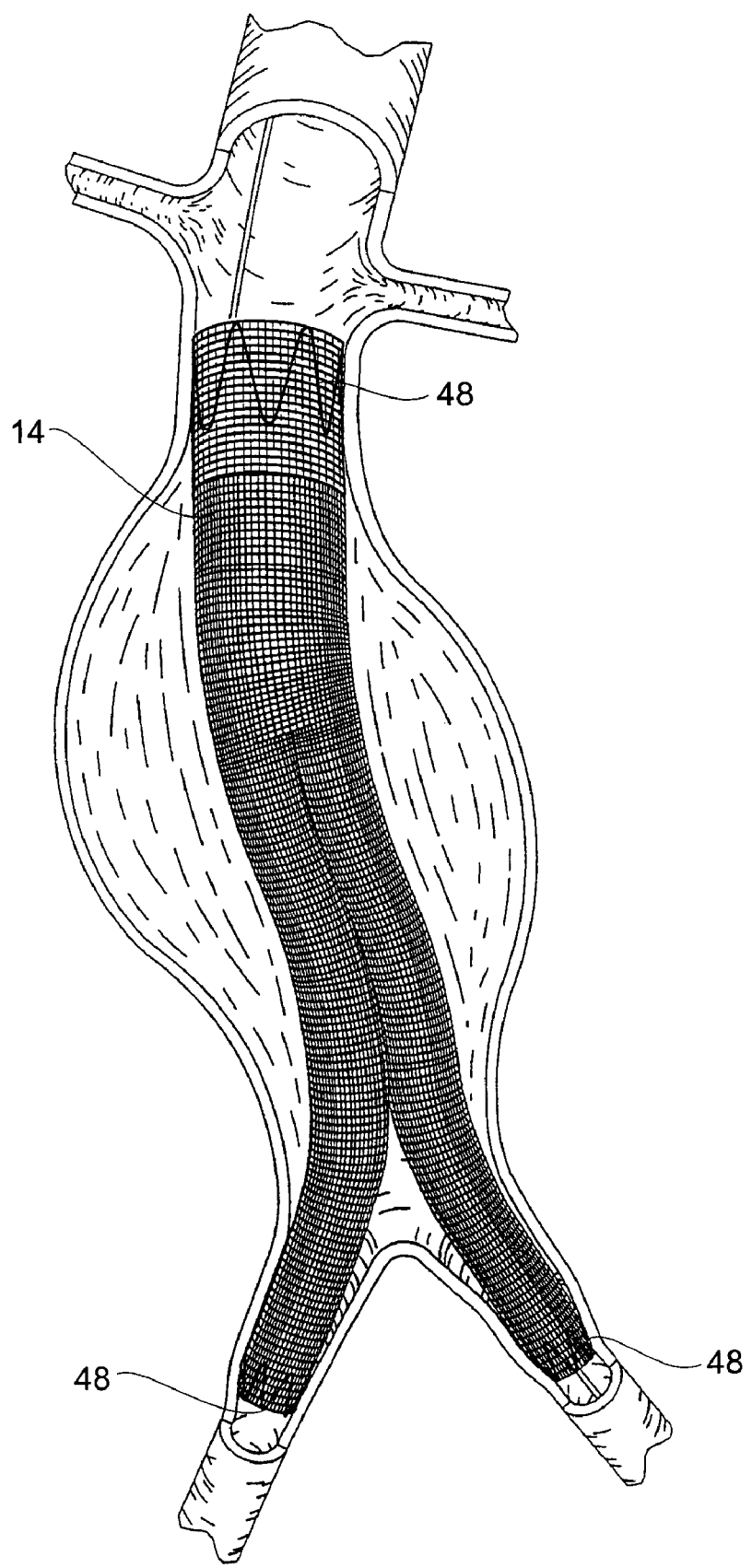
FIG. 4 is a perspective view of a bifurcated endovascular prosthesis after deployment by the prosthesis delivery catheter shown in FIG. 1A.

The prosthesis 14 can be sized and configured to be either straight or bifurcated form. FIG. 3 depicts a completely deployed straight prosthesis 14. FIG. 4 depicts a completely deployed bifurcated prosthesis.

Figure 2:
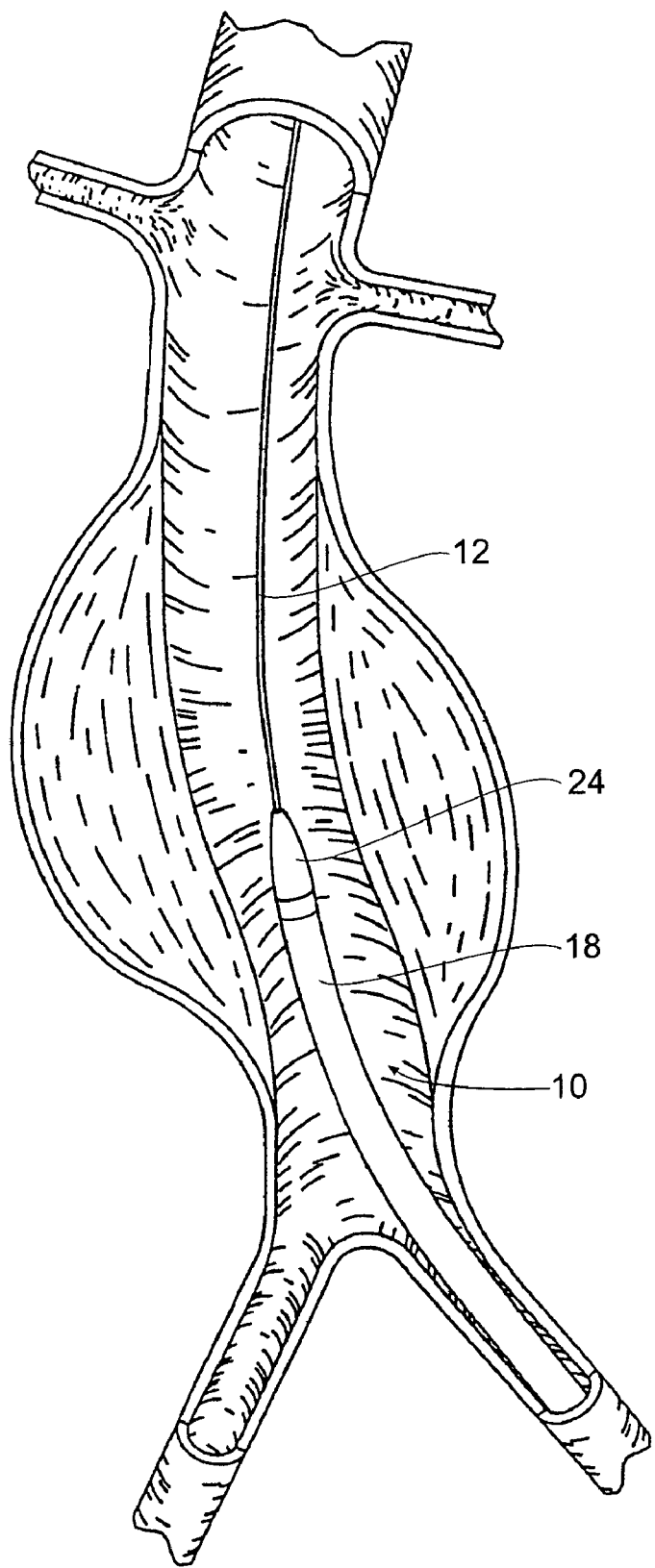
FIG. 2 is a perspective view of the prosthesis delivery catheter shown in FIG. 1A, being positioned within an abdominal aortic aneurysm.

For the purposes of illustration, FIG. 2 shows the targeted site as being within an abdominal aortic aneurysm. Of course, the targeted site can be elsewhere in the body.

As shown in FIGS. 1A and 1B, the catheter 10 comprises an inner assembly 16, an outer sheath 18, and a handle assembly 20. These components will now be individually described in greater detail.

A. The Inner Assembly

In the illustrated embodiment (see FIG. 5A), the inner assembly 16 comprises a central shaft 22, which functions as a carrier for the prosthesis. The inner assembly also includes a catheter tip component 24, a releasing means or mechanism 28 for retaining at least a portion of the prosthesis 14 in a radially compressed condition prior to deployment, a retaining means or mechanism 26 for maintaining the releasing means 28 in a desired relationship with the central shaft 22 during use, and a spacer 30.

Figure 5A:
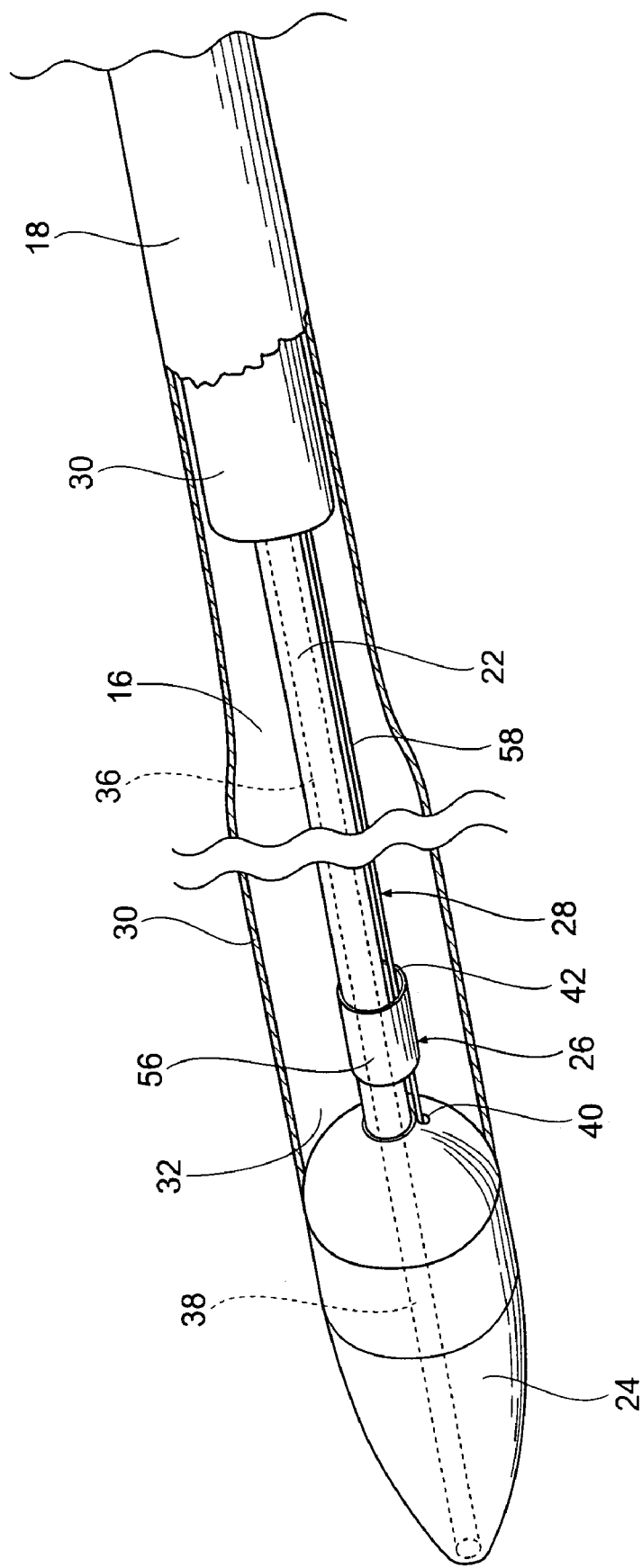
FIG. 5A is an enlarged perspective view, with portions broken away and in section, of the inner assembly which is located in the distal end of the prosthesis delivery catheter shown in FIG. 1A.

In the embodiment shown in FIG. 5A, the central shaft 22, the retaining means 26, the releasing means 28, and the spacer 30 are located within the confines of the outer sheath 18. In this respect, the outer sheath 18 functions as an enclosure for the prosthesis on the carrier. In this arrangement, the catheter tip component 24 is attached the distal end of the central shaft 22, and the distal end of the outer sheath 18 terminates adjacent the catheter tip component 24. Thus, the catheter tip component 24 extends outward beyond the outer sheath 18. The central shaft 22, the releasing means 28, and the outer sheath 18 connect to the handle assembly 20 at the proximal end of the catheter 10 (see FIG. 1A). In use (see FIG. 5B), the prosthesis 14 is contained in a cavity 32 defined between the central shaft 22 and the outer sheath 18 in the distal section of the catheter 10 (this arrangement is also shown in FIG. 1B).

The central shaft 22 extends from the handle assembly 20 (see FIG. 1A) to the catheter tip component 24. The central shaft 22 may be made, e.g., from stainless steel or other suitable medical materials including other metals or polymers. The central shaft 22 desirably has at least one lumen 36 (see FIG. 5A), with an inner diameter between 0.010 and 0.120 inches, preferably between 0.03 and 0.06 inches and most preferably between 0.04 and 0.05 inches.

As described, the central lumen 36 allows for the insertion of a guide wire 12 up to 0.038" diameter. The catheter tip component 24 also desirably has at least one lumen 38 (see FIG. 5A) configured to align with at least one lumen within the central shaft 22. This lumen 38 allows for the insertion of a guide wire 12 through the central shaft 22 and through the catheter tip component 24 (see FIG. 2). Typically this lumen will have an inner diameter between 010 and 0.120 inches, preferably between 0.03 and 0.06 inches and most preferably between 0.04 and 0.05 inches.

Preferably, the catheter tip component 24 is flexible and has a long, tapered distal end and a shorter, tapered proximal end. The maximum diameter of the catheter tip component 24 is approximately the same as the outside diameter of the distal end of the outer sheath 18. The distal end of the catheter tip component 24 provides a smooth tapered transition from the lumen 38 containing the guide wire 12 to the distal edge of the outer sheath 18. This feature aids in catheter insertion and navigation through tortuous anatomy over the guide wire 12.

The tapered section on the proximal end of the catheter tip component 24 prevents the catheter tip component 24 from inadvertently engaging the prosthesis 14, portions of the surrounding anatomy, or an introducer sheath or the like during removal of the catheter 10 from the body.

Still referring to FIG. 5A, the retaining means 26 holds the releasing means 28 in a desired, close relationship with the central shaft 22. The retaining means 26 orients the releasing means 28 along the axis to of the central shaft 22 and allows the releasing means 28 longitudinal movement in this axis. In the embodiment shown in FIGS. 5A, 5B, and 5C, the retaining means 26 includes a small hole or recess 40 in the proximal end of the catheter tip component 24 and a tube 56 having a diameter sufficiently large to accommodate both the central shaft 22 and the releasing means 28. In the embodiment shown in FIGS. 5A, 5B, and 5C, the tube 56 of the retaining means 26 is located over the central shaft 22 in alignment with and adjacent to the recess 40 on the catheter tip component 24. The tube 56 is attached to the central shaft 22 in a manner in that retains a crescent shape lumen 42 between the tube 56 and the central shaft 22. The releasing means 28 extends through this lumen 42 and into the recess 40.

Figure 5B:
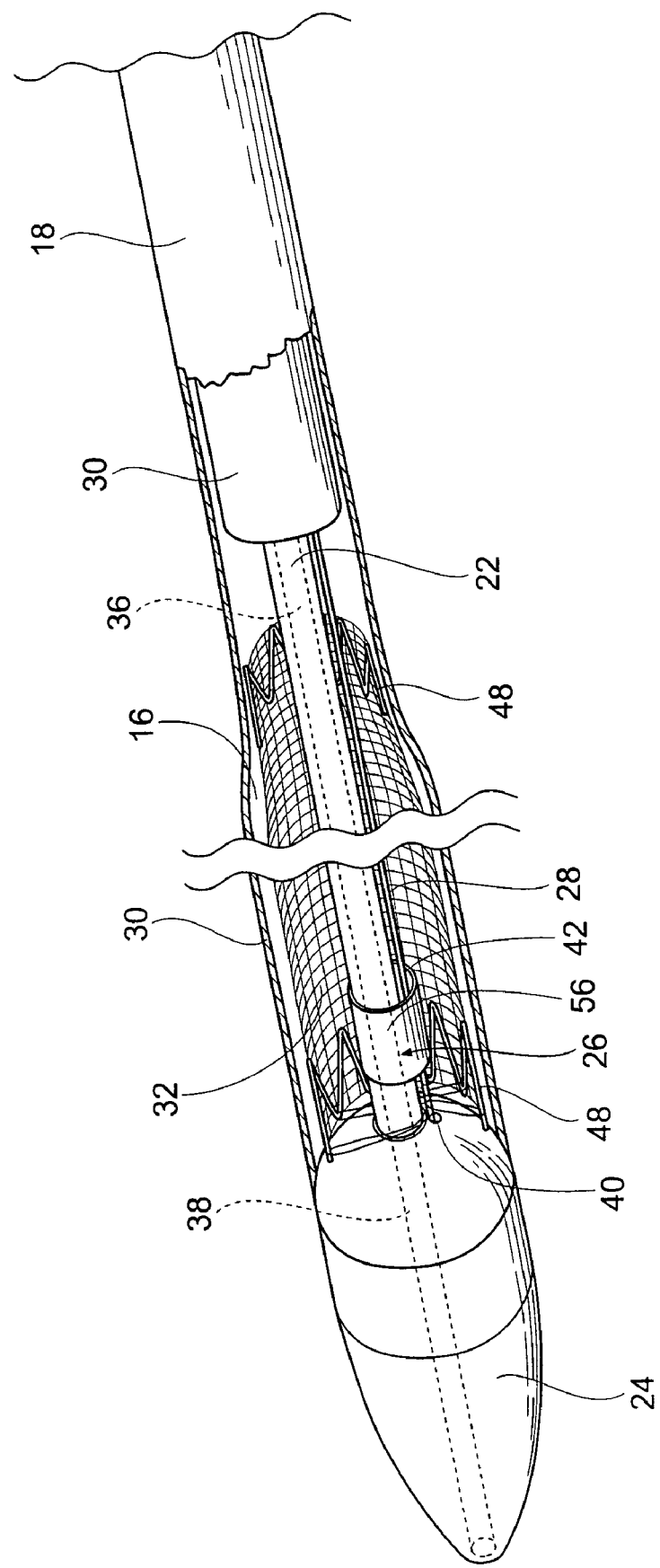
FIG. 5B is an enlarged perspective view, with portions broken away and in section, of the inner assembly which is located in the distal end of the prosthesis delivery catheter shown in FIG. 5A, showing a prosthesis retained in a collapsed condition by restraining means prior to deployment.

Returning to FIG. 5A, the spacer 30 provides support for the outer sheath 18 and, by occupying space within the outer sheath 18, reduces the amount of air entrapped within the catheter 10. The distal end of the spacer 30 desirably terminates adjacent the proximal end of the prosthesis 14 (as FIG. 5B shows). In this arrangement (see FIG. 5B), the cavity 32 containing the prosthesis 14 extends from the proximal end of the catheter tip component 24 to the distal end of the spacer 30. As FIG. 5A shows, the spacer 30 is positioned over the central shaft 22 and releasing means 28 and the proximal end of the spacer 30 is connected to the handle assembly 20. Typically, the spacer 30 can have an outer diameter slightly less than the inner diameter of the outer sheath 18. The spacer 30 can comprise a single lumen or an array of multiple lumens for passage of the various components within the spacer 30.

Figure 5C:
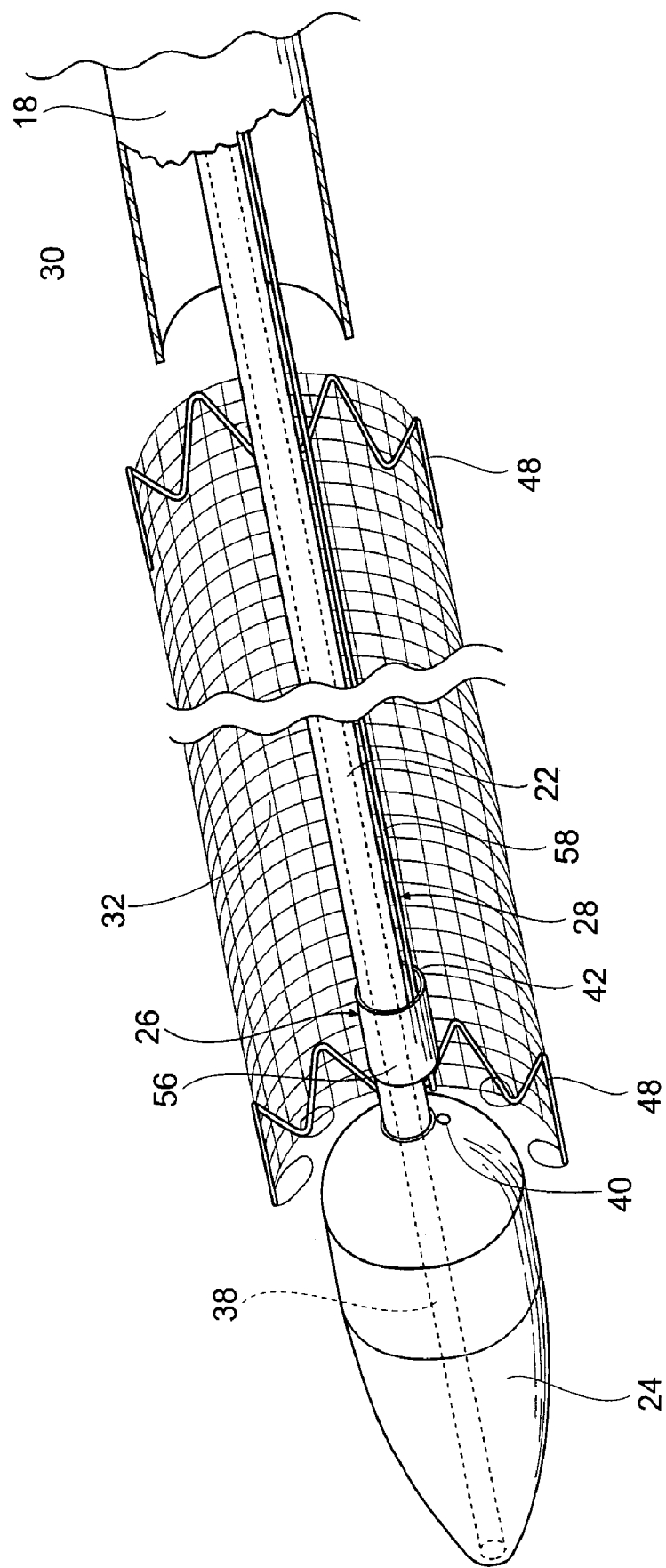
FIG. 5C is an enlarged perspective view, with portions broken away and in section, of the inner assembly which is located in the distal end of the prosthesis delivery catheter shown in FIG. 5A, showing the prosthesis in an expanded condition after removal of the restraining means.

The releasing means 28 holds the prosthesis 14 in a desired configuration prior to deployment (see FIG. 5B) and selectively releases the prosthesis 14 for deployment (see FIG. 5C). In the illustrated embodiment, the proximal end of the releasing means 28 is connected to an actuator or control button or knob 46 in the handle assembly 20 (see FIG. 1A). As FIG. 5B shows, the releasing means 28 extends along the outside of the central shaft 22, through the inside of the spacer 30, and continues distally through the inside of the prosthesis 14. The releasing means 28 passes through the prosthesis 14 and the retaining means 26.

As FIG. 5B best shows, the prosthesis 14 is retained by the releasing means 28 along the central shaft 22 in the cavity 32, which extends between the proximal end of the catheter tip component 24 and the distal end of the spacer 30. In the illustrated embodiment, the releasing means 28 includes a wire 58 that extends along the central shaft 22. The distal end of the wire 58 passes through the crescent shape lumen 42 of the retaining means 26, and is ultimately captured in the hole or recess 40 of the retaining means 26 in the proximal end of the catheter tip component 24. The distal end of the wire 58 is thereby kept in a desired relationship along the central shaft 22. The proximal end of the wire 58 is coupled to the control button 46, such that fore and aft movement of the button 46 advances the wire 58, respectively, distally and proximally.

As FIG. 5B shows (and which is further shown in more schematic form in FIGS. 11A, 11B, and 11C), the retaining means 28 includes sutures 44 and/or equivalent structures, which are attached to one or more stents 48 on the prosthesis 14. The sutures 44 are, in turn, looped around the wire 58 of the releasing means 28, when the wire 58 is in its distal-most position, as FIG. 5B shows. Proximal advancement of the wire 58 (using the control button 46) withdraws the wire 58 from the suture loops 44, as FIG. 5C shows.

In the illustrated embodiment (see FIG. 5B as well as FIGS. 11A, 11B, and 11C), the suture loops 44 are attached to one or more stents 48 at the distal end of the prosthesis 14. It should be appreciated, however, that suture loops 44 could be attached to stents 44 elsewhere in the prosthesis 14, and/or the other components of the prosthesis 14 as well.

The suture loops 44 and wire 56 of the embodiment of the releasing means 28 just described retain the prosthesis 14 to the central shaft (see FIG. 5B). The suture loops 44 and the wire 56 keep the prosthesis 14 from moving proximally as the outer sheath 18 is retracted. The releasing means 28 also keeps the stents 48 that are coupled to the suture loops 44 in a radially compressed condition as the outer sheath 18 is removed. The suture loops 44 and wire 56 prevent the distal end of the prosthesis 14 from self-expanding until the releasing means 28 has been withdrawn. In the illustrated embodiment, the withdrawal of the releasing means 28 is accomplished by operating the control button 46 to move the wire 58 proximally, withdrawing the wire 58 from the hole or recess 40 and away from the suture loops 44. Once the releasing means 28 is withdrawn, the restrained components of the prosthesis 14 are freed to self expand, as FIG. 5C shows.

As illustrated and described, the releasing means 28 is coupled to one restrained component of the prosthesis 14. It should be appreciated, however, that the releasing means 28 can be coupled to the prosthesis 14 at two or more restrained regions, so that withdrawal of the releasing means 28 frees the prosthesis at two or more restrained regions. It should also be appreciated that the releasing means 28 can comprise more than a single releasing element. For example, multiple, individual releasing wires 58 could be coupled to the prosthesis 14 at different regions, so that release of separate regions of the prosthesis 14 can be individually controlled.

B. The Outer Sheath

The outer sheath 18 also serves to restrain the stents 48 on the prosthesis 14 from expanding and allows for a control deployment of the prosthesis 14 within the body. In the illustrated arrangement, the outer sheath 18 is connected to an actuator or a collar or knob 50 on the handle assembly 20. As FIG. 5A shows, the outer sheath 18 extends distally over the spacer 30 and prosthesis 14 and terminates adjacent the proximal end of the catheter tip component 24. Typically, the outer sheath 18 can be made of a polymer tube and be free of structural reinforcement.

In the illustrated embodiment (see FIG. 5A), the outer sheath 18 is tapered due to the difference in outer diameters of the catheter tip component and the spacer 30. The larger diameter of the outer sheath 18 is intended to contain the main body of the prosthesis 14 and the smaller diameter would contain the leg portion or portions of the prosthesis 14, if present (as in the embodiment shown in FIG. 4). The smaller diameter continues proximally to the handle assembly 20. This tapered feature of the outer sheath 18 also allows for better blood circulation passed the catheter.

C. Handle Assembly

The handle assembly 20 provides the operator with longitudinal and rotational control of the catheter 10 within the body and provides access to the actuator or control means for deploying the prosthesis 14.

In the illustrated embodiment, the handle assembly 20 comprises a handle body 52 and the sliding knob or collar 50 which is connected to the proximal and the of the outer sheath 18, and the knob or button 46 which is attached to proximal end of the releasing means 28. In the illustrated embodiment, the central shaft 22 is captured within the handle and has a guide wire receiving luer 34 connected to its proximal end, which is located at the proximal end of the handle assembly 20. This design prevents the position of the prosthesis 14 from moving relative to the handle body 52 while the outer sheath 18 is retracted.

Figure 7:
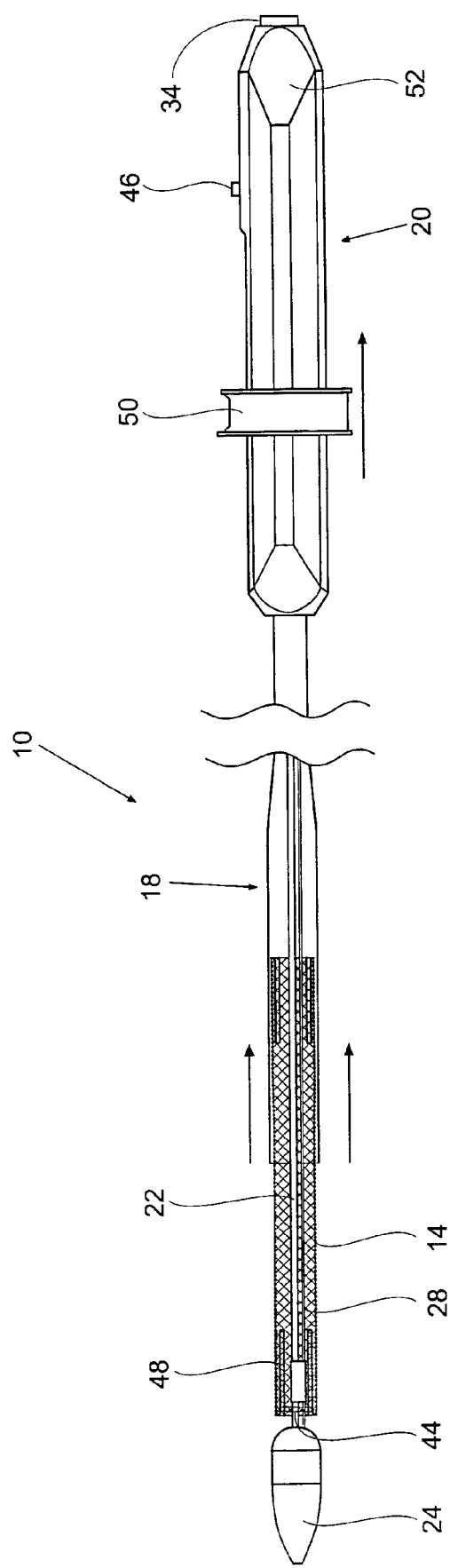
FIG. 7 is a side view, with portions broken away and in section, of the prosthesis delivery catheter shown in FIG. 6, showing the catheter retaining a prosthesis in a collapsed condition prior to deployment, the outer sheath being shown in a position withdrawn from the prosthesis.
Figure 8:
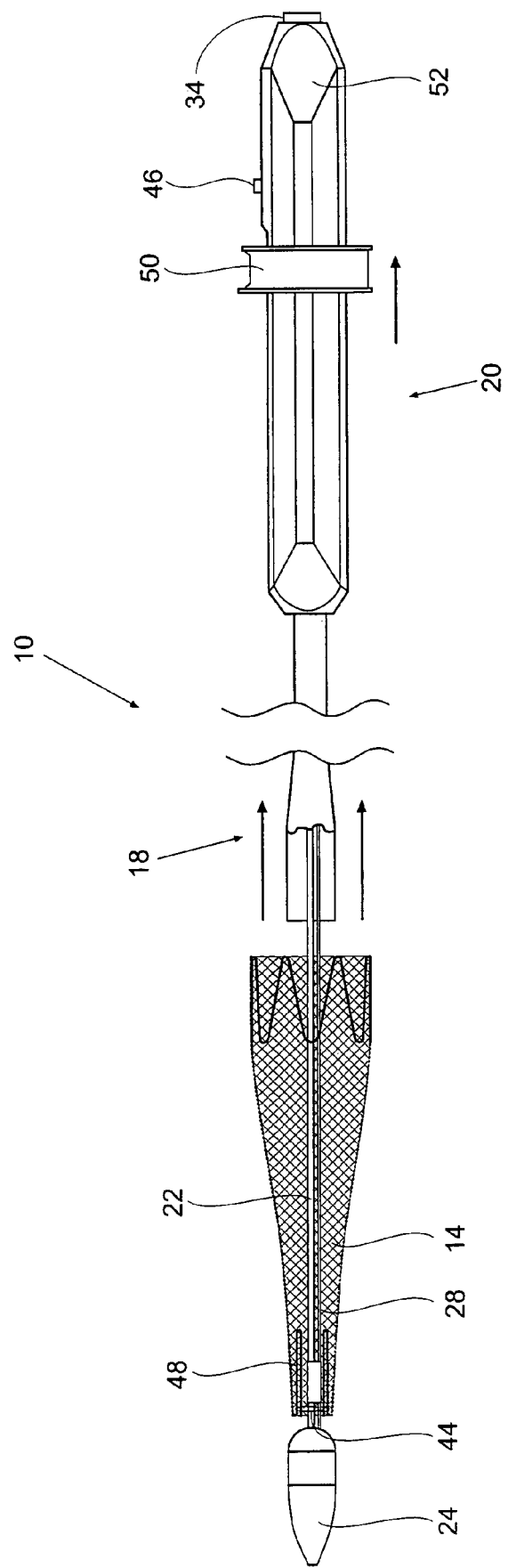
FIG. 8 is a side view, with portions broken away and in section, of the prosthesis delivery catheter shown in FIG. 7, showing the catheter retaining a prosthesis in a collapsed condition prior to deployment, with the pull wire still advanced to restrain radial expansion of the prosthesis.

To withdraw the outer sheath 18 from the prosthesis 14 (see FIGS. 6 and 7), the sliding knob 50 is moved proximally until the distal end of the outer sheath 18 is free of the prosthesis 14 (see FIG. 8). The portion or portions of the prosthesis 14 that are not coupled to the releasing means 28 (which, in the illustrated embodiment comprise the proximal region of the prosthesis 14) are free to self-expand, as FIG. 8 shows. However, the portions of the prosthesis 14 that are coupled to the releasing means 58 (which, in the illustrated embodiment comprise the distal region of the prosthesis 14) are still restrained from self-expansion, despite withdrawal of the outer sheath 18, as FIG. 8 also shows. The stent structure of the prosthesis 14 is thereby kept restrained closely against the central shaft tube 22 while the outer sheath 18 is retracted. The retaining means 26 prevents the prosthesis 14 from moving relative to the central tube 22 during retraction of the outer sheath 18, which potentially minimizes blood flow through the prosthesis 14 during the deployment process. Furthermore, as described, the prosthesis 14 is not "pushed out" of the catheter. The prosthesis 14 therefore need not have longitudinal stiffness or a stent structure with a "spine".

Figure 9:
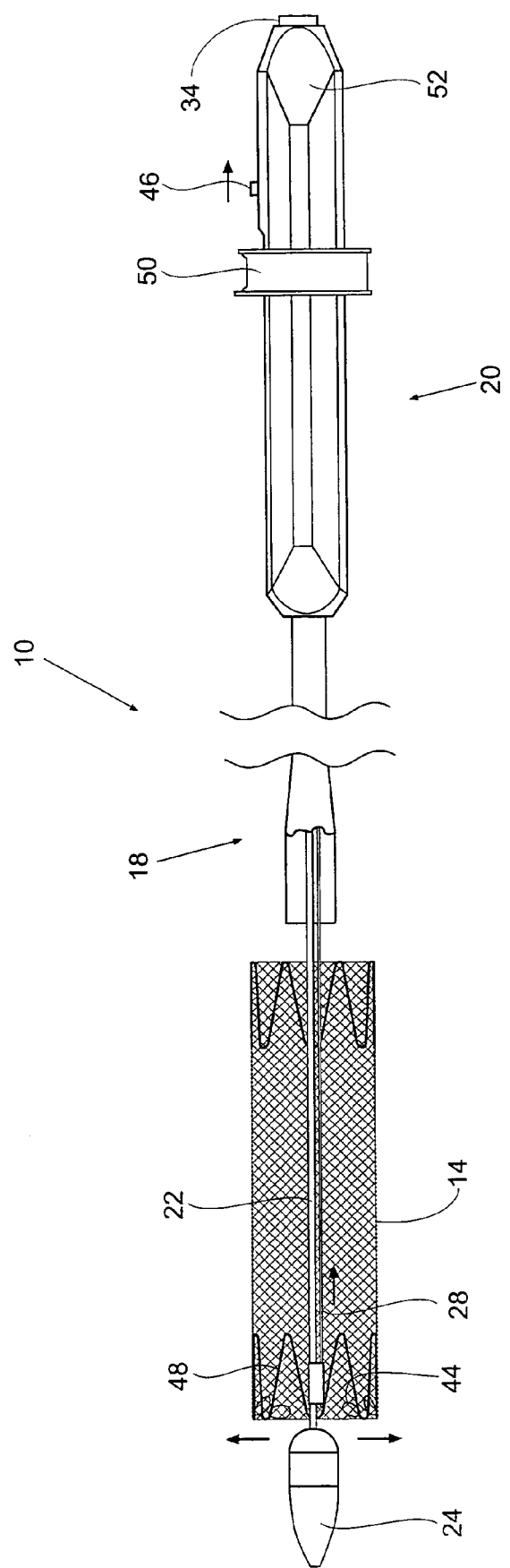
FIG. 9 is a side view, with portions broken away and in section, of the prosthesis delivery catheter shown in FIG. 8, showing the prosthesis in a radially expanded condition after actuation of the pull wire to remove the restraining means.

To withdraw the releasing means 28 (see FIGS. 8 and 9), the sliding button 46 is moved proximally until the distal end of the releasing means 28 is withdrawn from the restraining means 26. The prosthesis is thereby free to fully self-expand, as FIG. 9 and FIG. 5C show. As described, the prosthesis 14 is not released immediately from distal end to proximal end as the sheath 18 is withdrawn. As the outer sheath 18 is retracted, the prosthesis 14 is pulled in tension, which "stretches" the prosthesis to its proper length and stent spacing. The distal stent or stents 48 are released in a secondary operation, which follows the withdrawal of the outer sheath 18 (as shown in FIGS. 5C, 8, and 9). Final placement of distal end of the prosthesis 14 can therefore comprise a final step in the deployment process.

It should be appreciated that the knob 50 can comprise a separate component that is not part of the handle assembly 20, i.e., on the outer sheath 18.

II. Use of the Prosthesis Delivery Catheter

Figure 6:
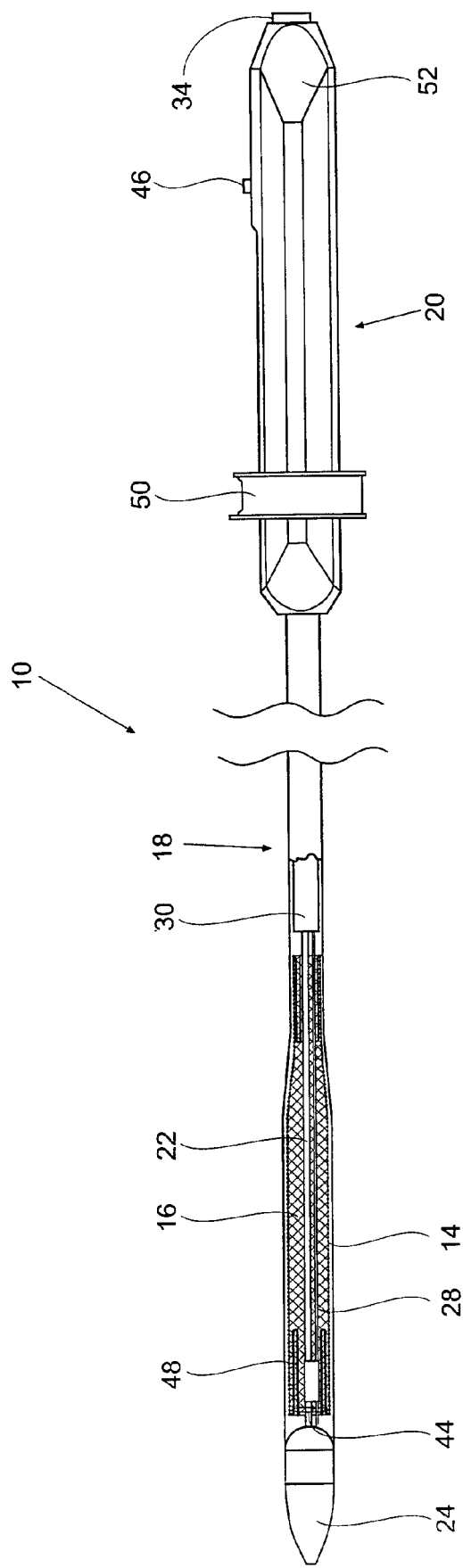
FIG. 6 is a side view, with portions broken away and in section, of the prosthesis delivery catheter shown in FIG. 1A, showing the catheter retaining a prosthesis in a collapsed condition prior to deployment, the outer sheath being shown in an advanced position over the prosthesis.

During use, the catheter 10 is navigated over the guide wire 12 to the desired location within the body (as FIG. 2 shows). In the illustrated embodiment, deployment of the prosthesis 14 is achieved in a two step process. First, by pulling the knob or collar 50 on the handle assembly 20 proximally, the outer sheath 18 is retracted and exposes the prosthesis 14 (as FIGS. 6 and 7 show). The unrestrained portion or portions of the prosthesis 14 self-expand, as FIG. 8 show. As FIGS. 6 and 7 show, during retraction of the outer sheath 18, the prosthesis 14 maintains its position relative to the central shaft 22 due to the releasing means 28 connected to the prosthesis 44.

Figure 10:
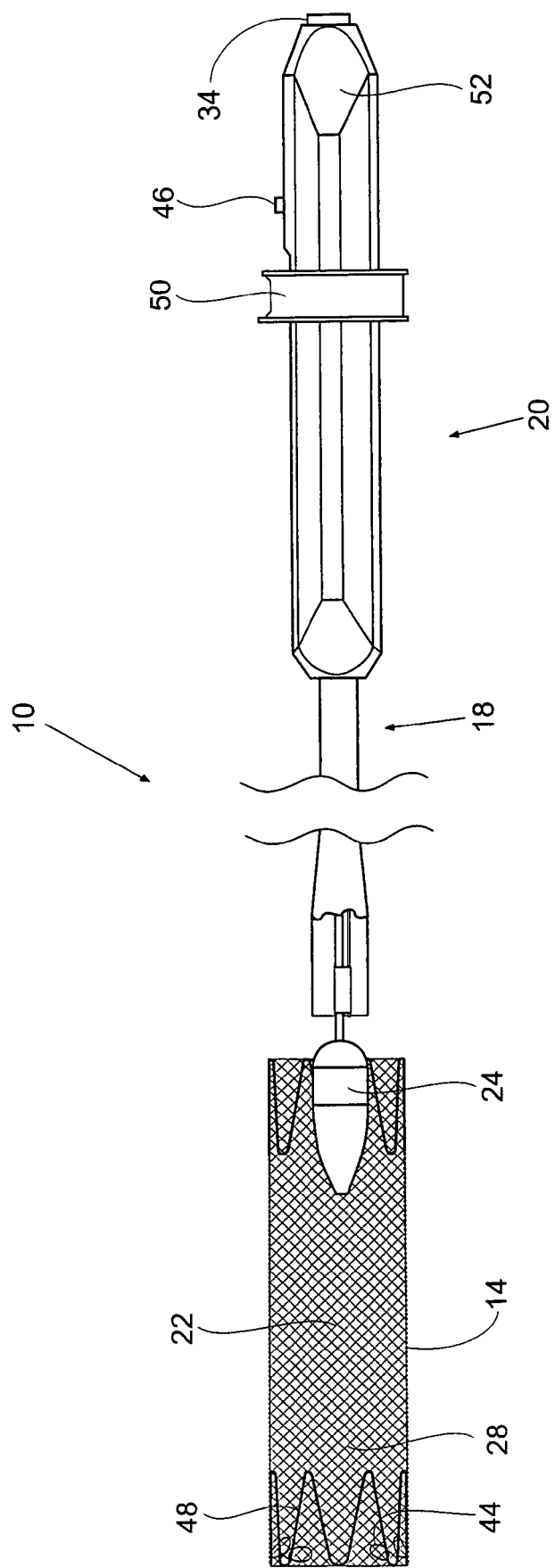
FIG. 10 is a side view, with portions broken away and in section, of the prosthesis delivery catheter shown in FIG. 9, showing the withdrawal of the catheter from the prosthesis after its deployment.

In the second step of the deployment process, following the withdrawal of the outer sheath 18, the control button or knob 46 on the handle assembly 20 is moved proximally (see FIGS. 8 and 9). This causes the distal end of the releasing means 28 to be withdrawn and allows the restrained stent or stents 44, and the prosthesis 14 as a whole, to self-expand radially (as FIGS. 5C and 9 show). The prosthesis 14 enlarges to contact the internal walls of the vessel or hollow body organ, as FIG. 3 shows. The catheter 10 can then be withdrawn (as FIG. 10 shows).

It should be appreciated that the withdrawal of the outer sheath 18 and the withdrawal of the releasing means 28 can be accomplished in a single step process. In this arrangement, a single activation mechanism can be jointly coupled to the outer sheath 18 and the releasing means 28, so that the outer sheath 18 and releasing means 28 are withdrawn in a single step.

III. Alternative Embodiments

Figure 11A:
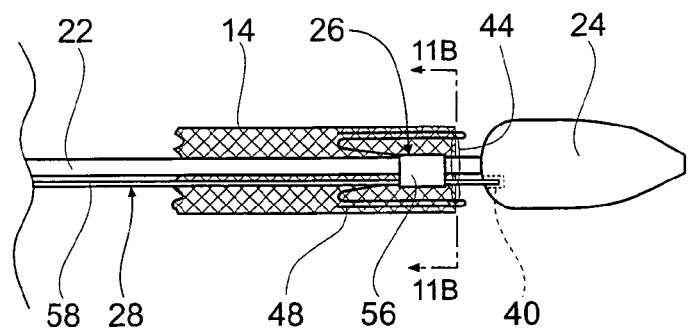
FIG. 11A is a simplified side view of the distal end of the prosthesis delivery catheter shown in FIG. 5B, with the outer sheath removed, showing the releasing means retaining the prosthesis in a restrained condition.
Figure 11B:
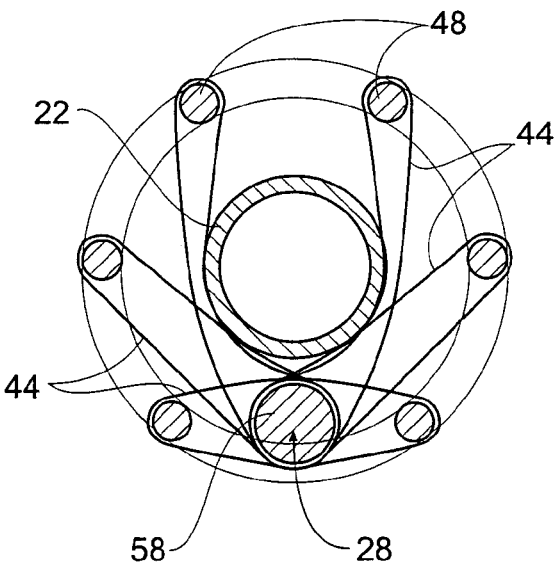
FIG. 11B is an end section view of the distal end of the prosthesis delivery catheter shown in FIG. 11A, taken generally along line 11B-11B in FIG. 11A.
Figure 11C:
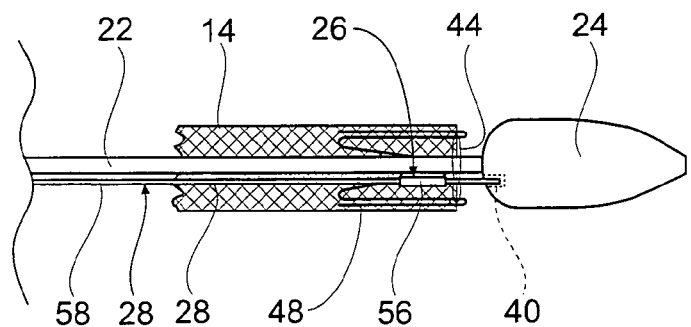
FIG. 11C is a simplified side view of the distal end of the prosthesis delivery catheter shown in FIG. 5B, with the outer sheath removed, showing an alternative embodiment of a restraining means for maintaining the releasing means in a desired orientation while retaining the prosthesis in a restrained condition.

In the embodiment shown in FIGS. 11A to 11C (as already described), the distal end of a movable component of the releasing means 28 (e.g., the wire 58) extends along the central shaft 22 in a manner prescribed and controlled by the restraining means 26, i.e., between a tube 56 carried by the central shaft 22 and a recess 40 located in the proximal end of the catheter tip component 24. It is in the region between the tube 56 and the recess 40, that a stationary component of the releasing means 28, which is attached to the prosthesis 14 (e.g., the suture loops 44), is operatively coupled to the movable component of the releasing means 28. Movement of the movable component 58 out of this region releases the stationary component 44. The overall objective of the restraining means 26 is achieved: the restraining means 26 serves to maintain the movable component 58 of the releasing means 28 in a desired operative alignment with the central shaft 22, as well as in a desired operative relationship with the stationary component 44 of the releasing means 28, such that quick and certain release of the prosthesis 14 occurs.

Figure 12A:
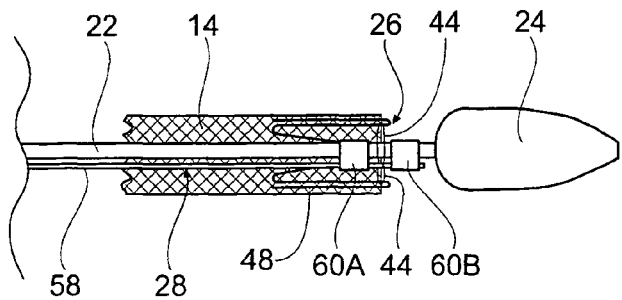
FIGS. 12A and 12B are simplified side views of the distal end of the prosthesis delivery catheter shown in FIG. 5B, with the outer sheath removed, showing other alternative embodiments of a restraining means for maintaining the releasing means in a desired orientation while retaining the prosthesis in a restrained condition, without reliance upon the catheter tip component.
Figure 12B:
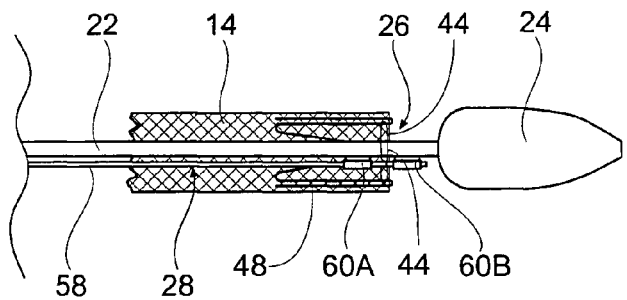

The releasing means 28 and the restraining means 26 can be variously constructed to meet this objective. For example, in the alternative embodiment shown in FIG. 12A, the distal end of the movable component 58 of the releasing means 28 extends along the central shaft 22 in a manner prescribed and controlled by the restraining means 26, i.e., between adjacent, spaced apart tubes 60A, and 60B, without dependence upon additional support by the catheter tip component 24. Each tube 60A and 60B surrounds the central shaft 22 in the same fashion as the single tube 56 shown in FIGS. 11A to 11C. The movable component 58 of the releasing means 28 is held in the region between the two tubes 60A and 60B in operative association with the stationary component 44 of the releasing means 28, and can be quickly and certainly withdrawn from this region to release the prosthesis 14. In a similar alternative arrangement (see FIG. 12B), the distal end of the movable component 58 of the releasing means 28 extends along the central shaft 22 between adjacent, spaced apart external tubes 62A and 62B, again without dependence upon additional support by the catheter tip component 24. In FIG. 12B, the tubes 62A and 62B project along the exterior of the central shaft 22, but do not surround it. Still, it should be appreciated that a single external support tube like tube 62A or 62B could, alternatively, be used in a hybrid combination with the recess 40 in the catheter tip component 24, if desired.

Figure 13A:
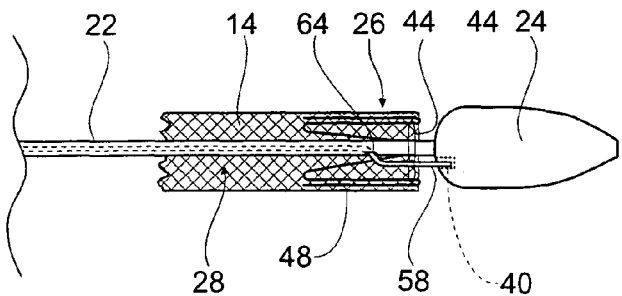
FIGS. 13A and 13B are simplified side views of the distal end of the prosthesis delivery catheter shown in FIG. 5B, with the outer sheath removed, showing other alternative embodiments of a restraining means for maintaining the releasing means in a desired orientation while retaining the prosthesis in a restrained condition, without reliance upon a tubular sleeve carried by the central shaft.
Figure 13B:
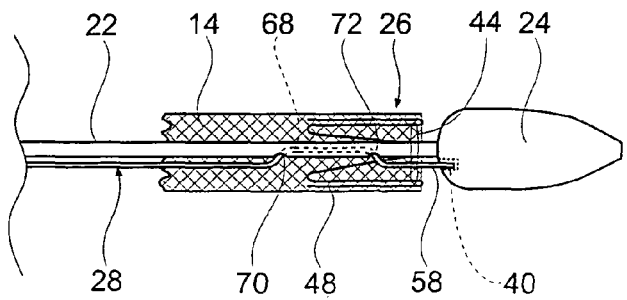

In another illustrative, alternative embodiment (see FIG. 13A), the distal end of the movable component 58 of the releasing means 28 extends within a lumen in the 66 central shaft 22, exiting through an aperture 64 in the shaft 22 and into a recess 40 in the catheter tip component 24. The movable component 58 of the releasing means 28 is held in the region between the aperture 64 and the recess 40 in operative association with the stationary component 44 of the releasing means 28, and can be quickly and certainly withdrawn from this region to release the prosthesis 14. In a similar alternative arrangement (see FIG. 13B), the distal end of the movable component 58 of the releasing means 28 extends within a lumen 68 the central shaft 22 between adjacent, spaced apart apertures 70 and 72. The movable component 58 exits the aperture 72 and enters a recess 40 in the catheter tip component 24. The movable component 58 of the releasing means 28 is held in the region between the aperture 72 and the recess 40 in operative association with the stationary component 44 of the releasing means 28, and can be quickly and certainly withdrawn from this region to release the prosthesis 14.

Figure 14A:
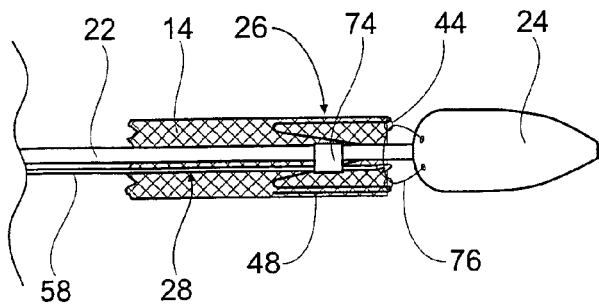
FIGS. 14A and 14B are simplified side views of the distal end of the prosthesis delivery catheter shown in FIG. 5B, with the outer sheath removed, showing other alternative embodiments of a releasing means with a cutting element for selectively releasing the prosthesis for use, together with an associated restraining means for maintaining the releasing means in a desired orientation for operation.
Figure 14B:
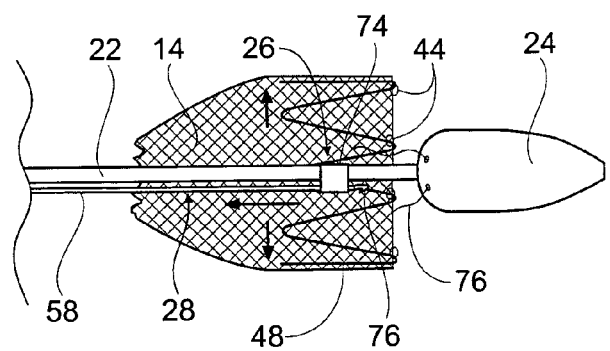

In yet another illustrative, alternative embodiment (see FIGS. 14A and 14B), the restraining means 26 includes a single tube 74 carried by the central shaft 22, through which the movable component 58 of the releasing means 28 passes. The tube 74 can comprise a surrounding tube of the type shown in FIG. 12A (as FIGS. 14A and 14B show) or an external tube of the type shown in FIG. 12B.

In this arrangement, the releasing means 28 includes a suture loop 76 carried by the proximal end of the catheter tip component 24 and a cutting element 78 carried on the distal end of the movable component 58 of the releasing means 28. The suture loop 76 passes through the suture loops 44 on the prosthesis 14, as well as through the cutting element 78. The cutting element 78 on the distal end of the movable component 58 of the releasing means 28 extends along the central shaft 22 in a manner prescribed and controlled by the restraining means 26, i.e., through and beyond the tube 74, and in operative association with the suture loops 44 and 76, which, in this embodiment, comprise the stationary components of the releasing means 28. This occurs without dependence upon additional support by the catheter tip component 24. Withdrawal of the movable component 58 moves the cutting element 78 through the suture loop 76, cutting the suture loop 76 and releasing the prosthesis 14 (as FIG. 14B shows).

Figure 15A:
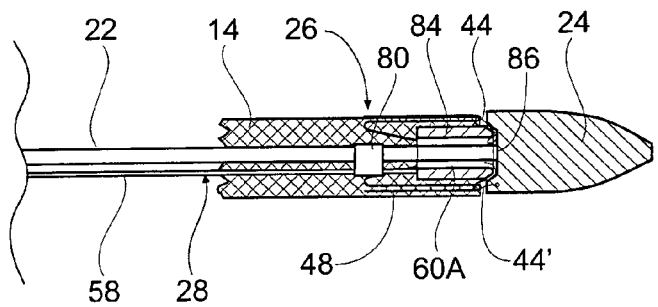
FIGS. 15A and 15B are simplified side views of the distal end of the prosthesis delivery catheter shown in FIG. 5B, with the outer sheath removed, showing other alternative embodiments of a releasing means with a wedge element for selectively releasing the prosthesis for use, together with an associated restraining means for maintaining the releasing means in a desired orientation for operation.
Figure 15B:
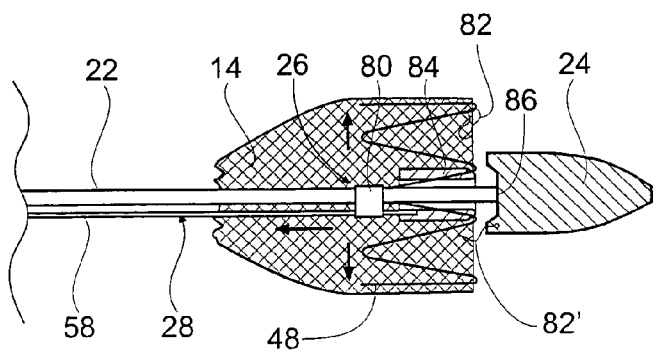

In yet another illustrative, alternative embodiment (see FIGS. 15A and 15B), the restraining means 26 includes a single tube 80 carried by the central shaft 22, through which the movable component 58 of the releasing means 28 passes. As the tube 74 shown in FIGS. 14A and 14B, the tube 80 can comprise a surrounding tube of the type shown in FIG. 12A (as FIGS. 15A and 15B show) or an external tube of the type shown in FIG. 12B.

In this arrangement, the releasing means 28 includes a wedge element 84 carried on the distal end of the movable component 58 of the releasing means 28. The wedge element 84 nests within a mating wedge surface 86 formed in the proximal end of the catheter tip component 24. Advancement of the movable component 58 moves the wedge element 84 into the registration within the wedge surface 86 (as FIG. 15A shows) and out of registration with the wedge surface 86 (as FIG. 15B shows). The releasing means 28 in this arrangement further includes alternative embodiments of suture loops 82 or 82', which are pinched between the wedge element 84 and the wedge surface 86 when the element 84 and the surface 86 are in registration, as FIG. 15A shows. The embodiment of the suture loop 82 comprises a closed loop 82 carried by a prosthesis stent 48. The embodiment of the suture loop 82' comprises an open loop 82' carried by the proximal end of the catheter tip component 24 and looped through a prosthesis stent 48. When either embodiment of the suture loop 82 or 82' is pinched between the wedge element 84 and the indented surface 86, expansion of the prosthesis 14 is restrained (as FIG. 15A shows). When the movable component 58 of the releasing means 28 is advanced proximally, the wedge element 84 is freed from registration within the wedge surface 86, freeing the loops 82 or 82', thereby releasing the prosthesis 14 for expansion, as FIG. 15B shows.

The preferred embodiments of the invention are described above in detail for the purpose of setting forth a complete disclosure and for the sake of explanation and clarity. Those skilled in the art will envision other modifications within the scope and sprit of the present disclosure.

The above described embodiments of this invention are merely descriptive of its principles and are not to be limited. The scope of this invention instead shall be determined from the scope of the following claims, including their equivalents.

We claim:

1. An apparatus for delivering a prosthesis comprising
a catheter sized and configured for introduction into a hollow body organ or blood vessel, the catheter having a distal end,
a carrier on the distal end sized and configured to carry the prosthesis during introduction of the catheter,
a release mechanism on the distal end being operable to retain the prosthesis on the carrier, the release mechanism also being operable to selectively release the prosthesis from the carrier for deployment in the hollow body organ or blood vessel, wherein at least part of the release mechanism is located inside of the prosthesis prior to deployment,
an enclosure mechanism on the distal end being operable to enclose the prosthesis on the carrier, the enclosure mechanism also being independently operable from said release mechanism to selectively expose the prosthesis on the carrier, to thereby enable the release of the prosthesis from the carrier in response to selective operation of the release mechanism, and
at least one actuator coupled to the release mechanism and the enclosure mechanism to selectively operate the release mechanism and the enclosure mechanism.

2. The apparatus according to claim 1, wherein the release mechanism comprises at least one suture loop in contact with the prosthesis and a releasing wire, wherein the suture loop is configured to prevent at least a portion of the prosthesis from self-expanding until the suture loop is no longer in contact with the releasing wire.

* * * * *